United States Patent [19]

Erpenbach et al.

[11] Patent Number: 4,985,383

[45] Date of Patent: Jan. 15, 1991

[54] PROCESS FOR REMOVING METALLIC CORROSION PRODUCTS FROM A CONTAMINATED CATALYST SOLUTION PRODUCED ON CARBONYLATION OF METHANOL AND/OR METHYL ACETATE AND/OR DIMETHYL ETHER

[75] Inventors: Heinz Erpenbach, Cologne; Winfried Lork, Erftstadt; Andreas Seidel, Cologne; Peter Prinz, Hürth, all of Fed. Rep. of Germany

[73] Assignee: Hoechst Aktiengesellschaft, Frankfurt am Main, Fed. Rep. of Germany

[21] Appl. No.: 470,945

[22] Filed: Jan. 26, 1990

[30] Foreign Application Priority Data

Feb. 10, 1989 [DE] Fed. Rep. of Germany ....... 3903909

[51] Int. Cl.$^5$ .................. B01J 38/68; B01J 31/40; C07C 51/54; C07C 51/12
[52] U.S. Cl. ........................ 502/24; 502/33; 560/232; 562/519; 562/890; 562/891
[58] Field of Search .............. 502/24, 22, 33; 422/22; 562/522, 519; 560/232

[56] References Cited

U.S. PATENT DOCUMENTS

| | | | |
|---|---|---|---|
| 3,887,489 | 6/1975 | Fannin et al. | 423/22 |
| 4,007,130 | 2/1977 | Leach et al. | 502/12 |
| 4,440,570 | 4/1984 | Erpenbach et al. | 423/22 |
| 4,442,304 | 4/1984 | Erpenbach et al. | 562/232 |
| 4,521,526 | 6/1985 | Hoffman | 502/24 |
| 4,578,367 | 5/1986 | Hoffmann | 502/24 |
| 4,746,640 | 5/1988 | Erpenbach et al. | 502/24 |

FOREIGN PATENT DOCUMENTS

| | | |
|---|---|---|
| 0032525 | 10/1980 | European Pat. Off. . |
| 0073342 | 7/1982 | European Pat. Off. . |
| 0074912 | 3/1983 | European Pat. Off. .............. 502/33 |
| 0156253 | 2/1985 | European Pat. Off. . |
| 0240703 | 2/1987 | European Pat. Off. . |
| 0265140 | 4/1988 | European Pat. Off. . |

*Primary Examiner*—Paul E. Konopka
*Attorney, Agent, or Firm*—Connolly & Hutz

[57] ABSTRACT

In a process for removing the metallic corrosion products from a contaminated catalyst solution produced on carbonylation of methanol and/or methyl acetate and/or dimethyl ether and containing carbonyl complexes of noble metals from group VIII of the Periodic Table of the elements, quaternary organo-phosphorus compounds as organic promoters, metallic corrosion products and acetic acid, acetic anhydride, ethylidene diacetate and, in some cases, undistillable organic compounds, the catalyst solution is treated with water, the noble metal carbonyl complex and the undistillable organic compounds, if present, being precipitated, while the organic promoter and the metallic corrosion products remain in solution; the aqueous phase is separated from the precipitated noble metal carbonyl complex and the organic promoter is extracted from the aqueous phase using $C_4$-$C_8$-alkanols, the promoter is recovered by evaporating the extractant, the promoter is recombined with the precipitated nobel metal carbonyl complex and with the undistillable organic compounds, if present, and the purified catalyst solution is recycled into the process after addition of acetic acid and/or acetic anhydride; finally, the aqueous phase with the metallic corrosion products is purged.

6 Claims, No Drawings

PROCESS FOR REMOVING METALLIC CORROSION PRODUCTS FROM A CONTAMINATED CATALYST SOLUTION PRODUCED ON CARBONYLATION OF METHANOL AND/OR METHYL ACETATE AND/OR DIMETHYL ETHER

The invention relates to a process for removing metallic corrosion products from a contaminated catalyst solution produced on carbonylation of methanol and/or methyl acetate and/or dimethyl ether and containing 0.5–15% by weight of carbonyl complexes of noble metals from group VIII of the Periodic Table of the elements, 20–70% by weight of quaternary organophosphorus compounds as organic promoters, 2–15% by weight of metallic corrosion products and 13–75% by weight of acetic acid, acetic anhydride, ethylidene diacetate and, in some cases, undistillable organic compounds.

The catalyst solution circulated in the carbonylation of methanol and/or methyl acetate and/or dimethyl ether is contaminated both by undistillable organic compounds which are formed in the process and are described as resins or tars, and by enrichment of metallic corrosion products such as iron, nickel, chromium and molybdenum. A rise in the concentration of the metallic corrosion products affects, in addition to the catalyst circulation, the course of the carbonylation by the formation of undesired by-products, for example acetone, carbon dioxide and methane.

Whereas the purification of the catalyst systems employed in carbonylation processes by removal of undistillable organic compounds has already been described a number of times, little is known so far about the recovery of rhodium and/or noble metal complexes from catalyst solutions contaminated with metallic corrosion products.

Thus, in German Offenlegungsschrift 2,358,410 (US-A-3,887,489), the rhodium-containing catalyst solution, which was obtained by mixing a rhodium component and an iodine component, usually hydrogen iodide or an alkyl iodide, in the presence of CO, is freed from the corrosion products Fe, Ni, Cr and Mo by precipitating the rhodium component by heating with stirring and, if appropriate, with addition of an alkanol having 1–5 carbon atoms at a temperature of 100°–190° C. and separating it from the corrosion products which remain in solution.

The same catalyst solution described above, which can also contain iridium in place of rhodium, is purified according to DE No. 2,659,173 A1 by removal of metallic corrosion products in such a way that it is treated with strongly acidic cation exchanger resins at temperatures of 0°–120° C. The resins are in the H form and bind the corrosion products, whereas the Rh-containing catalyst complex remains in solution.

EP 0,265,140 Aclaims a process in which the contaminated catalyst solution, which also contains a lithium component in addition to a rhodium component, is purified by removal of metallic corrosion products in such a way that it is treated with a cation exchanger in the Li form. The use of the cation exchanger in the Li form prevents a reduction in the Li content of the solution, since mainly the corrosion products are bound on the ion exchanger.

The methods described for the removal of metallic corrosion products are not applicable to the purification and recovery of the noble metal carbonyl complex and of the organic promoters from the catalyst solution contaminated during the carbonylation of methanol and/or methyl acetate and/or dimethyl ether.

In the methods known from the literature, the catalyst solutions to be purified originate in particular from carbonylation processes for the sole manufacture of acetic acid from methanol and CO. For an optimized course of the reaction, these processes demand water contents of up to about 15% by weight in the reaction mixture; organic undistillable compounds do not arise in this case. Moreover, the catalyst systems used do not absolutely require an organic promoter, and in particular not in such a high concentration as in the case of the simultaneous manufacture of acetic acid and acetic anhydride or also of acetic anhydride alone. The catalysts employed in the manufacture of acetic acid/acetic anhydride and the undistillable organic compounds which may in some cases arise in the process are water-insoluble and would therefore precipitate in the said processes. The production of acetic anhydride in an aqueous system under the conditions of a carbonylation is not possible.

The use of ion exchangers for purifying a catalyst solution employed under anhydrous conditions leads in the case of the present invention, in addition to a partial adsorption of undistillable organic compounds on the exchanger resin, also to an exchange of the rhodium-containing complex ion from the catalyst solution. As a result, the exchanger is inactivated more rapidly, and losses of the expensive rhodium catalyst occur. Moreover, the high content of promoter salt in the catalyst solution shows that it is necessary to remove the corrosion products without losses of not only rhodium but also promoter salt.

The present invention avoids the disadvantages demonstrated in the reported state of the art and describes a process which makes it possible in a simple manner by means of extractive methods to reprocess the catalyst solution employed in the carbonylation of methanol and/or methyl acetate and/or dimethyl ether and contaminated in the course of the process with metallic corrosion products, in such a way that the noble metal complex can be recovered without loss and the organic promoters can be recycled to the catalyst circulation, while the metallic corrosion products are separated off.

In particular, the invention comprises treating the catalyst solution with water, whereupon the noble metal carbonyl complex and the undistillable organic compounds, if present, are precipitated, while the organic promoter and the metallic corrosion products remain in solution, separating the aqueous phase from the precipitated rare metal carbonyl complex and extracting the organic promoter from the aqueous phase using $C_4$–$C_8$-alkanols, recovering the promoter by evaporating the extractant, recombining the promoter with the precipitated noble metal carbonyl complex and the undistillable organic compounds, if present, and recycling it as catalyst solution into the process after addition of acetic acid and/or acetic anhydride, and purging the aqueous phase with the metallic corrosion products.

Furthermore, the process according to the invention can preferably and selectively comprise (a) carrying out the treatment of the contaminated catalyst solution with water at 10°–100° C., and (b) employing 3–100 parts by weight of water per part by weight of contaminated catalyst solution.

The catalyst solution contaminated with metallic corrosion products originates from a reaction mixture which flows out of the carbonylation reactor and is separated by distillation into the desired end products acetic acid and acetic anhydride as well as unconverted, circulated starting materials on the one hand and the catalyst solution obtained as the bottom product on the other hand. A part stream of this catalyst solution contaminated in the course of time is taken from the catalyst circulation and freed according to the invention from the metallic corrosion products.

The contaminated catalyst solutions contain, as the noble metal, in general rhodium, iridium, palladium and/or ruthenium which are in the form of carbonyl complexes such as, for example, $[CH_3P(C_4H_9)_3]_2[Rh(CO)I_5]$, $[CH_3P(C_4H_9)_3]Rh(CO)I_4]$ or $[CH_3P(C_4H_9)_3][Rh(CO)_2I_2]$. The catalyst solutions also contain, as organic promoters, preferably one or more of the following organo-phosphorus compounds:

Tetrabutylphosphoniumiodide, tri-n-butyl-methyl-phosphonium iodide, trioctyl-methyl-phosphonium iodide, tri-lauryl-methyl-phosphonium iodide and/or triphenyl-methyl-phosphonium iodide.

The part stream taken off is advantageously added with stirring to water heated to, for example, 50° C. While the noble metal carbonyl complex and, if present, the undistillable organic compounds precipitate, the organic promoter is dissolved together with the metallic corrosion products in the water phase. The aqueous phase is separated from the precipitated noble metal complex and, for recovery of the promoter salt, subjected to an extractive treatment with, for example, n- or i-butanol or isoamyl alcohol. After evaporation of the extractant, the organic promoter remains which is then recombined with the catalyst complex, which has been precipitated and freed of metallic corrosion products, and undistillable organic compounds, if present, and recycled with added acetic acid and/or acetic anhydride into the carbonylation zone for re-use as catalyst solution. The metallic corrosion products are purged with the aqueous phase.

EXAMPLE 1

For removing the metallic corrosion products, 1000 g of catalyst solution of the composition 5.51% by weight of rhodium carbonyl complex $[CH_3P(C_4H_9)_3][Rh(CO)_2I_2]$ ($\hat{=}55.1$ g = 0.90% by mass of Rh), 53.72% by weight of methyl-tri-n-butylphosphonium iodide, 1.5% by weight of iron, 0.28% by mass of nickel, 0.24% by weight of chromium, 0.03% by weight of molybdenum and 29.4% by weight of a mixture of acetic acid, acetic anhydride and ethylidene diacetate are taken from the catalyst circulation of the methanol/methyl acetate carbonylation and introduced with stirring in the course of 30 minutes into 5000 ml of water at 80° C., the rhodium carbonyl complex precipitating. The stirrer is then turned off. After a settling time of 1.5 hours, the rhodium carbonyl complex has settled on the bottom of the vessel, so that the aqueous phase can be separated off by siphoning without filtration. For recovery of the promoter, the aqueous phase is then extracted by shaking with three times 1000 m of n-butanol. From the n-butanol phase, 522.7 g of methyl-tri-n-butylphosphonium iodide, corresponding to a yield of 97.3%, are recovered after evaporating off the n-butanol.

The carbonyl complex which has settled in the stirred vessel is combined with the recovered promoter salt and 14.5 g of fresh salt and, after making up to 1000 g with an acetic acid/acetic anhydride/ethylidene diacetate mixture, added again as regenerated catalyst solution to the catalyst circulation.

With the water phase freed from promoter salt, 14.60 g of iron, 2.791 g of nickel, 2.395 g of chromium and 0.29 g of molybdenum in the form of the iodides are purged from the process, after stripping off the n-butanol.

The contents, determined by analysis of the recycled catalyst solution, of 0.90% by weight of Rh, 0.06% by weight of iron, 0.004% by weight of nickel, 0.005% by weight of chromium and <0.001% by weight of molybdenum show the efficacy of the purification method. Without a loss of rhodium, the corrosion products iron, nickel, chromium and molybdenum are removed to the extent of 97.3%, 99.7%, 99.8% and >96.7% from the solution taken out of the catalyst circulation.

EXAMPLE 2

For removing the metallic corrosion products, 1000 g of catalyst solution of the composition 7.47% by weight of rhodium carbonyl complex $[CH_3P(C_4H_9)_3][Rh(CO)_2I_2]$ ($\hat{=}74.7$ g = 0.87% by weight of Rh), 55.45% by weight of methyl-tri-n-butylphosphonium iodide, 0.85% by weight of iron, 0.13% by mass of nickel, 0.15% by weight of chromium, 0.02% by weight of molybdenum and 30.7% by weight of a mixture of acetic acid, acetic anhydride and ethylidene diacetate are taken from the catalyst circulation of the methanol/methyl acetate carbonylation and introduced with stirring in the course of 30 minutes into 6000 ml of water at 45° C., the rhodium carbonyl complex precipitating. The stirrer is then turned off. After a settling time of 1.5 hours, the rhodium carbonyl complex has settled on the bottom of the vessel, so that the aqueous phase can be separated off by siphoning without filtration. For recovering the promoter, the water phase is then extracted by shaking with three times 1000 ml of isoamyl alcohol. From the isoamyl alcohol phase, 544.0 g of methyl-tri-n-butyl-phosphonium iodide, corresponding to a yield of 98.1%, are recovered after evaporating off the isoamyl alcohol.

The carbonyl complex which has settled in the stirred vessel is combined with the recovered promoter salt and 10.5 g of fresh salt and, after making up to 1000 g with an acetic acid/acetic anhydride/ethylidene diacetate mixture, added again as regenerated catalyst solution to the catalyst circulation.

With the water phase freed from the promoter salt, 8.10 g of iron, 1.25 g of nickel, 1.47 g of chromium and 0.19 g of molybdenum in the form of the iodides are purged from the process after stripping off the isoamyl alcohol.

The contents, determined by analysis in the recycled catalyst solution, of 0.87% by weight of Rh, 0.04% by weight of iron, 0.005% by weight of nickel, 0.003% by weight of chromium and <0.001% by weight of molybdenum show the efficacy of the purification method. Without loss of rhodium, the corrosion products iron, nickel, chromium and molybdenum are removed to the extent of 95.3%, 96.2%, 98.0% and >95.0% from the solution taken out of the catalyst circulation.

EXAMPLE 3

For removing the metallic corrosion products, 1000 g of catalyst solution of the composition 10.96 M-% of rhodium carbonyl complex $[CH_3P(C_4H_9)_3]_2[Rh(CO)I_5]$ ($\hat{=}109.6$ g = 0.94% by weight of Rh), 51.99 M-% of methyl-tri-n-butylphosphonium iodide, 0.62% by weight of iron, 0.11% by weight of nickel, 0.14% by weight of chromium, 0.02% by weight of molybdenum and 32.1% by weight of a mixture of acetic acid, acetic anhydride and ethylidene diacetate are taken from the catalyst circulation of the dimethyl ether carbonylation and introduced with stirring in the course of 30 minutes into 4500 ml of water at 60° C., the rhodium carbonyl complex precipitating. The stirrer is then turned off. After a settling time of 1.5 hours, the rhodium carbonyl complex has settled on the bottom of the vessel, so that the aqueous phases can be separated off by siphoning without filtration. For recovering the promoter, the water phase is then extracted by shaking with three times 1000 ml of n-octanol. From the n-octanol phase, 508.5 g of methyl-tri-n-butylphosphonium iodide, corresponding to a yield of 97.8%, are recovered after evaporating off the n-octanol.

The carbonyl complex which has settled in the stirred vessel is combined with the recovered promoter salt and 11.4 g of fresh salt and, after making up to 1000 g with an acetic acid/acetic anhydride/ethylidene diacetate mixture, added again as regenerated catalyst solution to the catalyst circulation.

With the water phase freed from promoter salt, 6.08 g of iron, 1.07 g of nickel, 1.34 g of chromium and 0.19 g of molybdenum in the form of the iodides are purged from the process, after stripping off the n-octanol.

The contents, determined by analysis in the recycled catalyst solution, of 0.94% by weight of Rh, 0.012% by weight of iron, 0.0025% by weight of nickel, 0.006% by weight of chromium and <0.001% by weight of molybdenum show the efficacy of the purification method. Without losses of rhodium, the corrosion products iron, nickel, chromium and molybdenum are removed to the extent of 98.1, 97.7, 95.7 and >95.0% from the solution taken out of the catalyst circulation.

We claim:

1. A process for removing metallic corrosion products from a contaminated catalyst solution produced on carbonylation of methanol, methyl acetate, dimethyl ether or mixtures thereof, the contaminated catalyst solution containing 0.5-15% by weight of carbonyl complexes of noble metals, 20-70% by weight of quaternary organo-phosphorous compounds as organic promotors, 2-15% by weight of metallic corrosion products and 13-75% by weight of acetic acid, acetic anhydride, and ethylidene diacetate, which comprises treating the catalyst solution with water to precipitate the noble metal carbonyl complex while the organic promotor and the metallic corrosion products remain in solution, separating the aqueous phase from the precipitated noble metal carbonyl complex and extracting the organic promotor from the aqueous phase using $C_4$-$C_8$ alkanols, recovering the promotor by evaporating the extractant, recombining the promotor with the precipitated noble metal carbonyl complex and recycling it as a catalyst solution into the process after addition of acetic acid, acetic anhydride or mixtures thereof, and purging the aqueous phase from the metallic corrosion products.

2. The process as claimed in claim 1, wherein the treatment of the contaminated catalyst solution with water is carried out at 10°-100° C.

3. The process as claimed in claim 1, wherein 3-100 parts by weight of water are employed per part by weight of contaminated catalyst solution.

4. A process for removing metallic corrosion products from a contaminated catalyst solution produced on carbonylation of methanol, methyl acetate, dimethyl ether or mixtures thereof containing 0.5-15% by weight of carbonyl complexes of noble metals, 20-70% by weight of quaternary organo-phosphorous compounds as organic promotors, 2-15% by weight of metallic corrosion products and 13-75% by weight of acetic acid, acetic anhydride, ethylidene diacetate and undistillable organic compounds, which comprises treating the catalyst solution with water to precipitate the noble metal carbonyl complex and the undistillable organic compounds while the organic promotor and the metallic corrosion products remain in solution, separating the aqueous phase from the precipitated noble metal carbonyl complex and extracting the organic promotor from the aqueous phase using $C_4$-$C_8$-alkanols, recovering the promotor by evaporating the extractant, recombining the promotor with the precipitated noble metal carbonyl complex and the undistillable organic compounds and recycling it as catalyst solution into the process after the addition of acetic acid, acetic anhydride or mixtures thereof, and purging the aqueous phase with the metallic corrosion products.

5. The process as claimed in claim 4, wherein the treatment of the contaminated catalyst solution with water is carried out at 10°-100° C.

6. The process as claimed in claim 4, wherein 3-100 parts by weight of water are employed per part by weight of contaminated catalyst solution.

* * * * *